United States Patent
Durniak

(10) Patent No.: US 6,979,336 B2
(45) Date of Patent: Dec. 27, 2005

(54) SYSTEM AND METHOD FOR DELIVERING BIOLOGICAL MATERIALS TO A PROSTHESIS IMPLANTATION SITE

(75) Inventor: Todd D. Durniak, Ft. Wayne, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 391 days.

(21) Appl. No.: 10/106,627

(22) Filed: Mar. 26, 2002

(65) Prior Publication Data

US 2003/0187513 A1    Oct. 2, 2003

(51) Int. Cl.$^7$ .............................................. A61B 17/58
(52) U.S. Cl. ..................................................... 606/92
(58) Field of Search .......................... 623/23.19, 22.12, 623/22.39, 23.62, 23.2; 606/94, 92, 102, 606/93, 86, 62–64

(56) References Cited

U.S. PATENT DOCUMENTS

| | | | |
|---|---|---|---|
| 4,274,163 A | | 6/1981 | Malcom et al. |
| 4,399,814 A | * | 8/1983 | Pratt et al. ..................... 606/94 |
| 4,593,685 A | * | 6/1986 | McKay et al. ................. 606/94 |
| 4,888,024 A | | 12/1989 | Powlan |
| 5,116,377 A | | 5/1992 | Skripitz et al. |
| 5,133,772 A | | 7/1992 | Hack et al. |
| 5,156,606 A | * | 10/1992 | Chin ........................... 606/86 |
| 5,343,877 A | | 9/1994 | Park |
| 5,376,123 A | | 12/1994 | Klaue et al. |
| 5,501,687 A | * | 3/1996 | Willert et al. ................. 606/94 |
| 5,658,350 A | | 8/1997 | Carbone |
| 5,683,395 A | * | 11/1997 | Mikhail ........................ 606/86 |
| 5,755,720 A | * | 5/1998 | Mikhail ........................ 606/94 |
| 5,954,771 A | | 9/1999 | Richelsoph et al. |
| 2003/0097184 A1 | * | 5/2003 | Mitsugi et al. .......... 623/23.19 |

* cited by examiner

Primary Examiner—Eduardo C. Robert
(74) Attorney, Agent, or Firm—Maginot, Moore & Beck

(57) ABSTRACT

In one embodiment of the invention, a method is provided including the steps of preparing an opening in the bone sized to receive a prosthesis therein and then inserting an apertured temporary implant into the opening. A fluent material is then injected into the temporary implant so that the material exudes from the apertures into contact with the bone surrounding the temporary implant. The temporary implant is then removed to make way for implanting the prosthesis into the bone opening. The fluent material can be a biological, biocompatible or bioactive material, such as a composition adapted to permanently fill voids and irregularities in the bone or a composition adapted to promote bone growth. In another embodiment, an implant assembly includes an apertured sleeve adapted to be permanently implanted within the bone opening, but providing apertures for injecting a fluent material into the opening. The sleeve defines a cavity for receiving the distal portion of a prosthetic joint element, which can be fixed to the sleeve.

21 Claims, 2 Drawing Sheets

SYSTEM AND METHOD FOR DELIVERING BIOLOGICAL MATERIALS TO A PROSTHESIS IMPLANTATION SITE

BACKGROUND OF THE INVENTION

The present invention relates to systems and methods for improved fixation of prosthetic implants within a bone. More specifically, the invention concerns the introduction of biologic material to the implantation site that can enhance the implantation and fixation of the prosthesis within the bone.

Total hip arthroplasty, or hip replacement, is rapidly becoming a prevalent orthopedic procedure as the overall population ages. For instance, at present nearly a half a million hip replacements are performed worldwide on an annual basis.

The success rate for hip arthroplasty is very high, usually greater than 90%. The hip replacement can greatly improve the quality of life for the patient by dramatically reducing the pain and disability experienced by the patient. However, as with any artificial implant, hip implants are not without problems. One common problem is that the femoral implant loosens from the femoral canal over time. Although less frequent, the acetabular cup may also loosen or dislocate over time. If the loosening is serious enough, revision surgery may be necessary to repair or replace the prosthetic implants.

Prosthetic bone and joint implants, such as the femoral prosthesis discussed above, are typically mounted in one of two ways, i.e., using cementing and non-cementing techniques. With either approach, the medullary canal of the bone is prepared by some type of boring process. In the non-cementing techniques, the prosthesis is designed to provide a tight, interference fit with the prepared medullary canal. In addition, some prostheses are anchored in place by bone screws extending into the cortical bone surrounding the prepared canal.

Cementing techniques usually require the same type of preparation of the medullary canal as non-cementing techniques. Once the canal is prepared, a restrictor plug is typically inserted into the base of the medullary canal to contain bone cement applied into the canal. The cement is usually injected into the now plugged canal and the prosthesis inserted. The prosthesis is kept stationary until the cement has cured. In the case of cementing techniques, the prosthesis is smaller than the medullary canal, leaving ample room for a layer of bone cement between the prosthesis and the bone.

Much of the recent arthroplasty development has been in improving the bone cement material itself. The most typical bone cement is composed of a polymethylmethacrylate polymer. Other developments designed to enhance the effectiveness of the bone cement have been to provide a porous coating or a mesh on the prosthesis, to utilize different cement materials, such as thermoplastic polymer, or to utilize a cement impregnated with various biocompatible materials.

While the nature of the bone cement and cementing process has been the subject of much development, little attention has been paid to preparing the implantation site itself. It is believed that non-uniformities within the prepared medullary canal can decrease the effectiveness of any cementing or non-cementing fixation technique. Certainly, the typical candidate for total hip arthroplasty is an elderly patient. One common problem faced by the elderly patient is the reduction of bone density and a commensurate increase in bone brittleness. For instance, as illustrated in FIG. 1, a patient's femur 10 having a prepared femoral canal 12 may exhibit a significant non-uniformity over much of the canal. The bone surrounding the canal may yield voids 14 or general surface irregularities 16. Likewise, the acetabulum 20, and particularly its prepared socket 22, may also exhibit similar voids 24 and irregularities 26. Not only do these voids and irregularities pose an immediate fixation problem, they can also serve as locus for further degeneration of the bone surrounding the prepared canal 12 or socket 22.

It is therefore desirable to provide some means for addressing voids and irregularities, or general weakness, in bone into which a prosthesis is engaged, whether in a cementing or a non-cementing technique.

SUMMARY OF THE INVENTION

In order to address these needs, the present invention contemplates a system and method for introducing a fluent material into a bone opening to aid in securing a prosthesis within the opening. In one embodiment of the invention, a method comprises the steps of preparing an opening in the bone sized to receive the prosthesis therein and then inserting an apertured temporary implant into the opening. A fluent material is then injected into the temporary implant so that the material exudes from the apertures into contact with the bone surrounding the temporary implant. The temporary implant is then removed to make way for implanting the prosthesis into the bone opening.

In one aspect of the invention, the fluent material is a biocompatible or bioactive material. In one embodiment, the fluent material includes a composition adapted to permanently fill voids and irregularities in the bone. For instance, the composition can be selected from the group including a bone slurry, a bone substitute, a demineralized bone matrix, a bone paste and a bone cement. In another embodiment, the material includes a composition adapted to promote bone growth, such as a composition selected from the group including a bone growth factor, a platelet gel, a bone morphogenic protein and bio-resorbable materials. The type of fluent material selected depends upon the type or preparation necessary prior to implantation of the permanent prosthesis. Moreover, different fluent materials can be introduced simultaneously or sequentially through the temporary implant into the bone opening.

In certain embodiments, the fluent material is injected under pressure into the temporary implant. For certain fluent materials, injecting the material under pressure allows it to infiltrate irregularities and voids in the surrounding bone. For instance, in one aspect of the invention, a bone slurry is injected through the temporary implant so that is fills these irregularities and voids, thereby providing a uniform surface for receiving and fixing the permanent implant. In other instances, the fluent material can be a bone protein adapted to penetrate the surrounding bone and provide a vehicle for strengthening the bone and the fixation of the implant within the bone. In one feature of the inventive method, the fluent material is maintained under pressure for a period of time sufficient for the material to invade bone voids within the bone opening.

In another feature, where the fluent material is curable or settable, the temporary implant is maintained within the bone opening for a period of time sufficient to allow the material to at least partially cure in situ. The material may be maintained under pressure to keep in contact with the surrounding bone and to aid in the curing process. For some materials, the temporary implant is removed before the material is complete cured, such as where a bone cement or paste is utilized.

Other aspects of the inventive method contemplate the step of providing a seal adjacent the distal end of the temporary implant to retain the fluent material within the bone opening. The seal can be a bone cement plug situated within the bone opening below the temporary implant. Alternatively, the temporary implant itself can be configured with a seal at its distal end, which can be in the form of a flared portion of the implant or a sealing ring. In addition to the distal seal, a proximal seal can be provided at the proximal end of the temporary implant or at the proximal surface of the bone opening.

In another aspect of the invention, a method is provided for securing a prosthesis within a bone comprising the steps of preparing an opening in the bone sized to receive the prosthesis therein, filling voids in the bone at the bone opening, and then implanting the prosthesis into the bone opening. The step of filling voids in the bone can includes inserting an apertured temporary implant into the opening, injecting a curable material into the temporary implant so that the material exudes from the apertures into voids the bone, and then removing the temporary implant.

The present invention further contemplates a temporary implant for use in securing a prosthesis within an opening formed in a bone. The temporary implant can be particularly adapted to accomplish the methods described. In a preferred embodiment of the invention, the temporary implant includes a body sized for removable placement within the opening formed in the bone. The body can defining a fitting for engaging a device for injecting fluent material. The device can assume many forms, provided it is capable of injecting the fluent material, such as a bioactive material or a bone paste. Examples of such a device include a syringe or a pressurized injector known in the art. In certain embodiments, the fitting can be a Luer-type fitting, and can be removably mounted to the body.

In an important aspect of the invention, the body of the temporary implant further defines a number of apertures in communication between the fitting and an exterior surface of said body within the bone opening. The apertures provide a path for fluent material injected into the temporary implant to come into contact with the surrounding bone in the opening. The body can further define a cavity in fluid communication between the fitting and the number of apertures.

In one feature, the body of the temporary implant can include a lower sealing element at a distal portion thereof, in which the lower sealing element is configured to sealingly engage the bone opening. The lower sealing element can then prevent migration of the fluent material into portions of the bone not involved in the fixation of the prosthesis. In addition, the body can include an upper sealing element at a proximal portion thereof, with the upper sealing element also configured to sealingly engage the bone opening. These sealing elements can be in the form of flared surface on the body that project outwardly to engage the surface of the bone opening. The sealing elements can also include a seal ring construction.

In accordance with one feature of the invention, the number of apertures can be calibrated to optimize the imposition of the fluent to specific areas of the bone opening. For instance, the implant body can define a plurality of apertures distributed between proximal and distal portions of the body. The distribution of apertures can be concentrated in regions of the bone that may be more susceptible to voids and irregularities. The apertures can be provided in the form of elongated fenestrations.

In specific embodiments, the body of the temporary implant can be configured for placement within an opening formed in a femur to receive a femoral implant. In other embodiments, the body can be configured for placement within an opening formed in the acetabulum to receive an acetabular cup.

In yet another aspect of the invention, an implant assembly is provided for securement within an opening formed in a bone. In one aspect of this embodiment of the invention, a sleeve is provided that is formed by a cylindrical wall defining a cavity therein. The sleeve defines a plurality of apertures through the cylindrical wall that are in fluid communication between the bone opening and the cavity when the sleeve is disposed within the bone opening. The implant assembly further includes a joint prosthesis having a proximal end configured to mate with a complementary joint prosthesis. The joint prosthesis further includes an elongated distal end that is sized for a close fit within the cavity of the sleeve. In the preferred embodiment, the cavity is open at a proximal end of said sleeve (to receive the joint prosthesis) and closed at an opposite distal end (to close the cavity). The proximal end of the sleeve is configured to mate with a fluid injection device for injecting a fluent material into the sleeve prior to insertion of the joint prosthesis into the cavity.

In one aspect of this embodiment of the invention, the sleeve can be implanted within the bone opening and then the fluent material can be introduced into the bone opening through the apertures in the sleeve. The fluent material can include the materials noted above, depending upon the bone treatment desired. The fluent material can include a biocompatible cement that can be injected under pressure to exude from the apertures in the sleeve. With the cement occupying the sleeve cavity, the joint prosthesis can be inserted into the cavity. The bone cement will fill the space between the distal end of the prosthesis and provide a solid fixation of the prosthesis to the sleeve when the cement cures.

It is one object of the present invention to provide a system and method for delivering fluent materials to an implant fixation site in advance of introducing the implant. Another object is accomplished by features of the invention that allow a variety of biological, biocompatible and/or bio-active materials to be introduced into a bone opening to prepare the surrounding bone for implantation and fixation of a prosthesis. These and other objects, as well as certain benefits, of the invention will be appreciated upon consideration of the following written description taken together with the accompanying figures.

DESCRIPTION OF THE PREFERRED EMBODIMENTS

Figure 1:
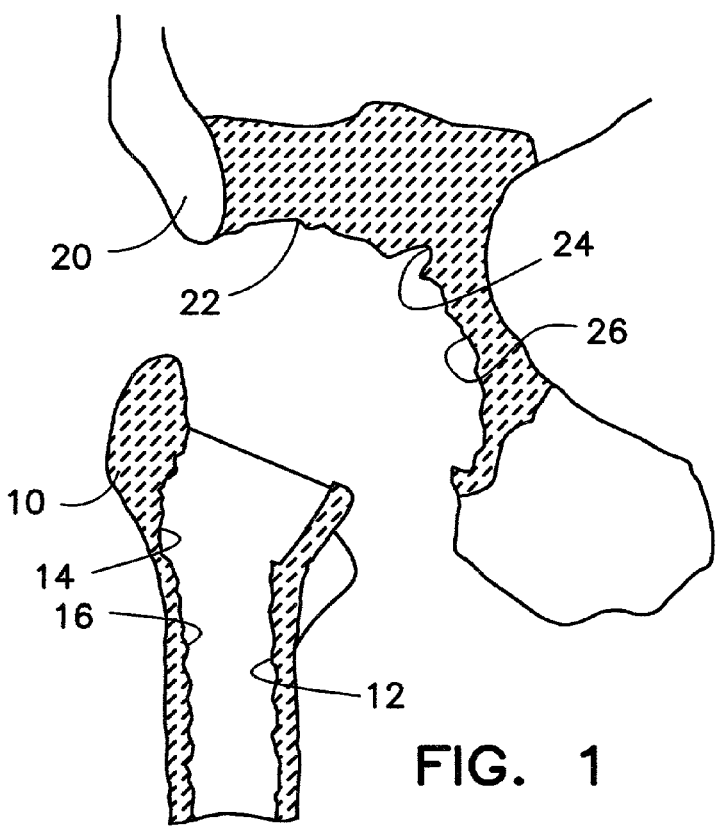
FIG. 1 is a partial cross-sectional view of the femur and acetabulum prepared for implantation of a hip prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a system and method for delivering biological material to a prepared implantation site. For instance, the invention has particular application for treatment of a prepared femoral canal, such as a canal 12 in a femur 10, as depicted in FIG. 1. In addition, the invention can be applied to a prepared acetabular socket 22. The femoral canal 12 or socket 22 can be prepared for a cementing or a non-cementing technique for implantation of the hip prosthesis components.

Figure 2:
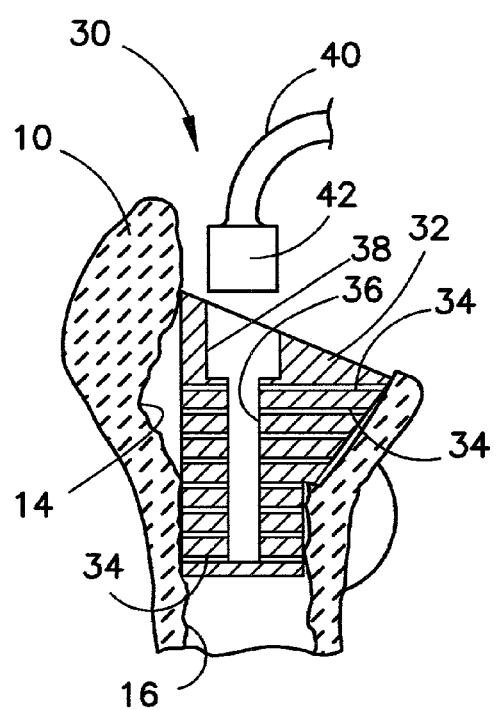
FIG. 2 is a partial cross-sectional view of the head of a femur with a biological material delivery system according to one embodiment of the present invention mounted within the prepared femoral canal.

Referring now to FIG. 2, a delivery system 30 is depicted that is mounted within the femoral canal 12. The delivery system 30 can include a temporary implant 32 having a body that is sized to easily fit within the prepared femoral canal 12. Preferably, the temporary implant 32 is dimensioned slightly smaller than the femoral canal 12, to thereby leave an annular region surrounding the implant for the introduction of a layer of a biological fluid.

The temporary implant 32 includes a plurality of apertures 34 communicating between the outside surface of the implant 32 facing the bone opening and an interior feed cavity 36. Preferably, the feed cavity 36 has a closed distal end and defines a mating cavity 38 at its proximal end. The mating cavity 38 can be configured to engage a fitting 42 of an injector component 40. In a specific preferred embodiment, the mating cavity 33 and fitting 42 can be configured as a Luer® fitting. The injector component 40 can comprise a syringe, or can include a flexible tube mated to a syringe or other type of device configured for injecting fluid under pressure.

In an application of the delivery system 30, the system can be used to inject bone slurry or a bone cement material into the prepared femoral canal 12. When applied under even slight pressure, the injected slurry or cement will pass through the feed cavity 36 and out of the implant 32 through the various apertures 34 to fill the voids 14 and/or irregularities 16 within the prepared canal. The provision of the large number of apertures 34 allows the fluid to be delivered where it is most required. For instance, the void 14 would likely require a greater quantity of material than some of the irregularities 16 at other locations within the femoral canal 12. In the illustrated embodiment of FIG. 2, three rows of apertures are in direct communication with the void 14, so that a significant quantity of the injected material will be directed into the void. It can be appreciated that the location and size of the apertures can be varied depending upon the biomaterial being injected and the anticipated treatment being rendered.

In accordance with a preferred embodiment of the invention, the material is injected and maintained under pressure so that it will be introduced into all of the irregularities, voids and interstices of the prepared bone site. The material is maintained under pressure a sufficient time for the material to fully impregnate the implantation site. Moreover, the pressure can be maintained to keep the material from flowing away from or out of the voids and irregularities.

For certain materials, the pressure is maintained for a sufficient time to allow the material to at least partially cure in situ. For instance, if a bone cement is being utilized to fill a void 14, the temporary implant 32 should be removed before the material cures completely because some of the cement will necessarily span from the void 14 through the aperture 34 and into the feed cavity 36. However, the cement should be sufficiently cured before the implant is removed so the cement will maintain its patency within the prepared site.

On the other hand, certain injectable fluids may not require curing. For instance, fluids containing bone growth factors, bone morphogenic proteins, or platelet gels, do not necessarily set or solidify. As an alternative, these biomaterials can be incorporated into a self-setting material, such as a gel, in order to help retain the materials within the prepared femoral canal 12 prior to and during insertion of the prosthesis. In the instance where the biomaterial does require setting, it is preferable to inject the material as deeply is possible into the prepared bone, particularly into the irregularities 26 and other microstructure. This biomaterial will then be retained within the bone once the prosthesis is finally implanted.

It can be further appreciated that the temporary implant provides a vehicle for the injection of different fluent materials into the bone opening. These different materials can be injected sequentially or simultaneously as appropriate. Preferably, fluent materials that do not require curing would be injected first, followed by the curable materials. For instance, it may be desirable to inject a bone morphogenic protein through the temporary implant to pre-treat the surrounding bone. A bone slurry can then be provided to fill irregularities and voids within the bone opening.

Figure 3:
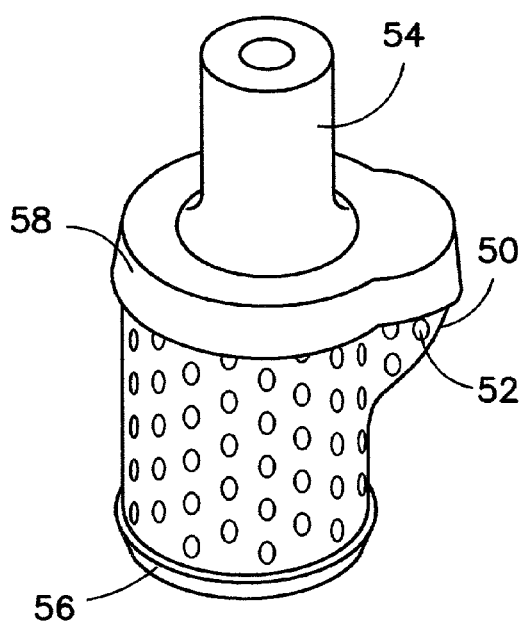
FIG. 3 is a side perspective view of a biological material delivery system in accordance with one embodiment of the present invention.

An alternative temporary implant 50, depicted in FIG. 3, is configured and shaped to fill the femoral canal 12 defined within the prepared femur. One preferred orientation and arrangement of the plurality of apertures 52 is illustrated in the figure. It should be understood that in the illustrated embodiment, the apertures 52 are discretely formed through the wall of the temporary implant 50. Alternatively, the implant can be constructed of a porous material that incorporates a web of interconnected interstices. For instance, the implant can be formed of a porous tantalum material known as Hedrocell®. Thus, fluid injected into the temporary implant 15 will flow through the interconnected interstices and exit the portion of the implant within the prepared canal.

In the embodiment illustrated in FIG. 3, the temporary implant 50 can include a fitting 54 that projects from the body of the implant. The fitting 54 can be integrally formed as part of the implant, or can be engaged or threaded within a central cavity defined in the implant. The fitting 54 can be configured to engage a tapered injector tip, or a flexible tube. At any rate, the fitting 54 provides means for engagement with an injector capable of pressure injection of the biological material through the implant into the femoral canal 12.

In a further aspect of this embodiment of the invention, the implant 50 can include sealing features for retaining the fluid within the bone opening. In one embodiment, this sealing feature can include lower and upper sealing rims 56 and 58, respectively, defined by the body of the implant. The purpose behind the sealing rims 56 and 58 is to produce a sealed cavity around the implant 50 to prevent flow of the injected fluid outside of the region to be treated. The rims can be formed as part of the implant 50 and therefore of the same material as the implant. In one embodiment, the rims 56, 58 can be formed by flaring the implant outward at the upper and lower portions. In an alternative embodiment, the sealing rims 56 and 58 can be in the form of flexible gaskets that readily conform to the wall of the femoral canal 12 below the apertures 52. The gaskets can be rubber seal rings disposed or retained within grooves formed in the temporary implant.

Figure 4:
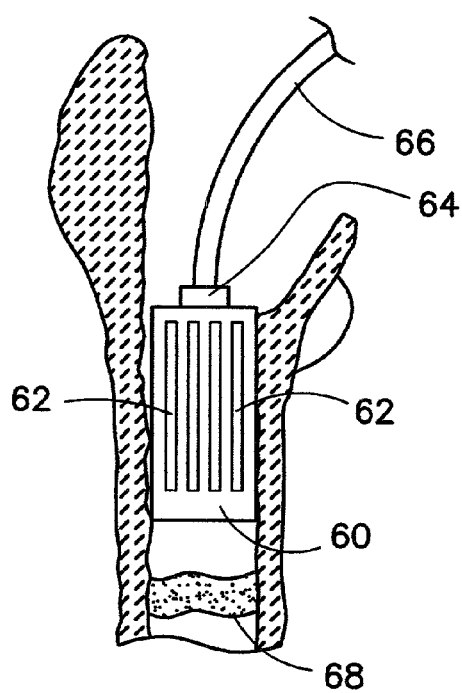
FIG. 4 is a side partial cross-sectional view of a femoral canal containing a delivery system according to a further embodiment of the present invention.

As a further alternative, the implant 50 can include only an upper sealing rim 58. Flow of the injected material beyond the distal end of the temporary implant 50 can be prevented by the introduction of a cement plug into the base of the femoral canal 12. For instance, as depicted in FIG. 4, a cement plug 68 can be placed into the canal in a conventional manner. The temporary implant 50 can then be placed within the canal 12 so that its distal end is directly proximate the cement plug 68.

Referring still to FIG. 4, an alternative embodiment of the invention is depicted in which a temporary sleeve 60 performs the delivery function. The sleeve 60 can include apertures in the form of an array of fenestrations or windows 62 that are configured for dispensing of pressured fluid from within the sleeve 60 outward into the prepared femoral canal 12. The sleeve 60 can include a fitting 64 to engage an injector component 66, similar to that described above.

The fenestration 62 in the temporary sleeve 60 of this embodiment may be preferable over the apertures 52 for certain types of biological material to be injected. For instance, if the material has a relatively low viscosity, it may be difficult to flow through small diameter openings, such as apertures 52. On the other hand, the greater area provided by the fenestrations 62 may facilitate flow of the low viscosity material into the known voids and irregularities.

In a further feature of the invention, the temporary implant 60 of FIG. 4 can be substantially cylindrical along its entire length. In this case, the implant is generally limited to delivering biological material to the substantially cylinder portion of the femoral canal 12, rather than to the portion at the head of the femur. The sleeve 60 can be provided with upper and lower sealing rims, such as the rims 56 and 58 shown in FIG. 3. One benefit provided by the cylindrical sleeve 60 is that the sleeve can be rotated when removal is desired. This rotation will help sever any material that has cured or partially cured within the fenestrations 62. To that end, the edges of the fenestrations can be relatively sharp to cleanly sever the material as the sleeve is rotated.

With each of the embodiments shown in FIGS. 2–4, the temporary implant 32, 50 or 60 is intended to be removed once the biological material has been injected into the site and cured or partially cured, if necessary. Once the fluid delivery or impregnation process has been completed, the temporary implant is removed and a permanent prosthesis is implanted. Again, the present invention can be used in conjunction with either cementing or non-cementing techniques without any effect on those techniques.

Figure 5:
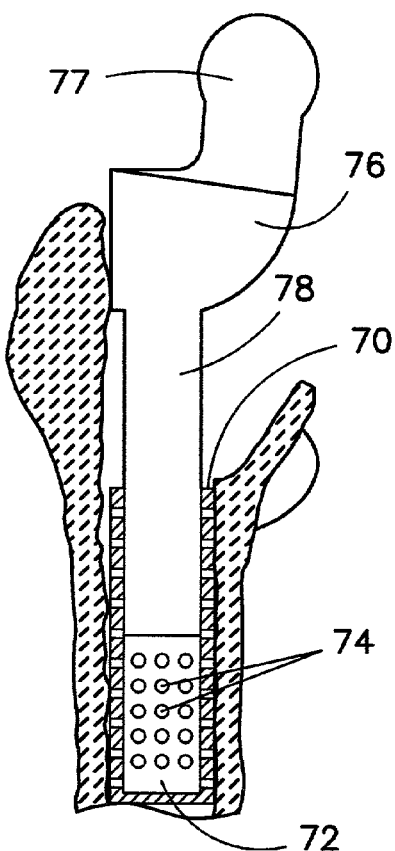
FIG. 5 is a side partial cross-sectional view of a prepared femur with a delivery sleeve and a modular implant in accordance with yet another embodiment of the present invention.

As an alternative, the delivery system can be incorporated as part of a permanently implanted modular prosthesis system. One embodiment of such a system is depicted in FIG. 5 as a modular sleeve 70 that is permanently disposed within the prepared femoral canal. The sleeve 70 can include a plurality of apertures 74 communicating with an enlarged central chamber 72. The sleeve 70 can alternatively include fenestrations, such as the fenestrations 62 of the sleeve 60 shown in FIG. 4.

In the illustrated embodiment, the chamber 72 is closed at its distal end and open at its proximal end. However, the chamber 72 can be open at both ends so that the sleeve 70 is essentially annular. In this case, a cement plug, such as the plug 68 shown in FIG. 4 can be situated distal of the modular sleeve 70.

Whether the sleeve 70 includes apertures or fenestrations, it still serves the same purpose—i.e. to provide a delivery system for a biological fluid into the prepared femoral canal 12. Thus, the sleeve 70 serves as a delivery device in the same manner as the temporary implants described above. The proximal end of the chamber 72 can be configured to engage a fitting for making connection to an injection device. For instance, the fitting 54 shown in FIG. 3 can be modified to removably fit within the top opening of the chamber, such as by way of a threaded engagement. The fitting can then be used to inject the appropriate biological material through the sleeve and into the prepared femoral canal. Depending upon the material being delivered through the modular sleeve 70, excess material may need to be removed from the chamber 72.

Once the femoral canal has been appropriately prepared, a modular joint element 76 can be implanted. Specifically, the joint element can include a proximal end 77 that is configured as an articulating element for the particular joint. The joint element also includes a stem 78 that is sized to fit within the chamber 72. In one embodiment, the stem 78 can form a press-fit engagement with the sleeve 70. In a preferred alternative embodiment of the invention, bone cement is disposed within the chamber 72 as the stem 78 is pushed into the chamber 72. As the stem enters the chamber, the bone cement flows through the apertures 74 into direct contact with surrounding femoral canal. In addition, a quantity of bone cement fills the annular space between the stem 78 and the interior wall of the chamber 72. As the stem 78 is pushed more deeply into the chamber, excess bone cement will eventually flow through the open proximal end of the chamber and into the femoral head region. If enough cement is provided, the cement will fully fill the femoral canal and completely surround both the modular sleeve 70 and the modular joint elements 76 to provide a solid fixation of the implant within the femur.

Figure 6:
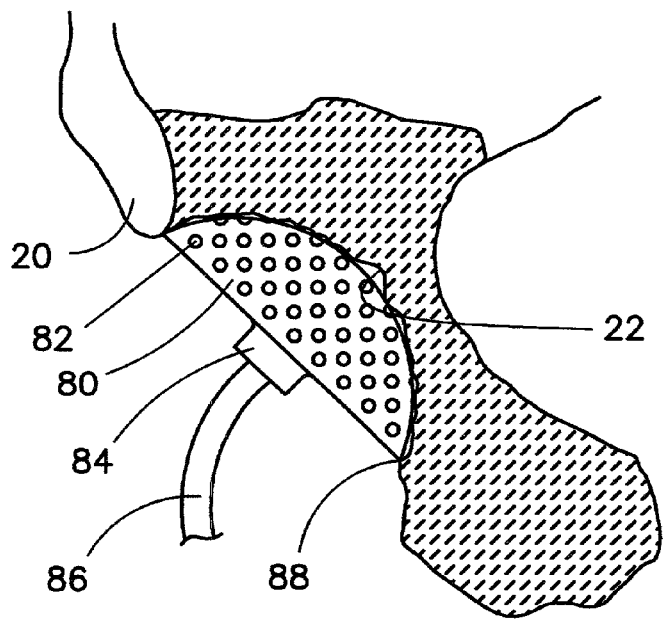
FIG. 6 is a side partial cross-sectional view of a prepared acetabular cup with a biological material delivery system in accordance with another embodiment of the invention.

This same technology can be applied to preparing the acetabular socket 22. Thus, as depicted in FIG. 6, the present invention contemplates a temporary cup 80 that includes a plurality of apertures 82. A fitting 84 can be connected to an injector element 86, again similar to that described above. The fitting can be permanently attached to the cup, or can be removably engaged, such as by a threaded engagement.

Fluid introduced through the fitting 84 can pass through a cavity within the cup and exude through the apertures 82. Preferably, the proximal edge 88 of the cup 80 is flared outward or includes some other sealing feature to help retain the cup within the acetabular socket 22. The cup 80 can be a temporary implant that is only used for injecting the biological material into the prepared acetabular socket. Alternatively, the cup can be a permanent implant to mate with the proximal end 77 of the modular joint element 76 of FIG. 5. When used as a permanent implant, the cup 80 may require cleaning after the biological material has been injected through the cup. In this case, the fitting 84 must be removable to expose the interior of the cup 80 to receive the ball end of a femoral prosthesis.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The temporary implants 30, 50, 60 and 80 contemplate a hollow cavity within the body of the implants. As an alternative, each of the apertures (34, 52, 82) or fenestrations (62) can be in direct communication with the inlet passageway at the inlet fitting. Where the cavity is retained, its dimensions can be modified. For instance, the cavity 36 can be enlarged so that the temporary implant 32 is in the form of a thin-walled apertured cylinder.

In accordance with the preferred embodiments, the temporary implants 30, 50, 60 and 80 or the permanent sleeve 72 provide an avenue for the introduction of a biologically compatible material to the implant situs. In one embodiment, the material includes a composition adapted to permanently fill voids and irregularities in the bone. The composition can be selected from the group of biomaterials including a bone slurry, a bone substitute, a demineralized bone matrix, a bone paste and a bone cement.

In addition to the void filling materials, the biologically compatible material introduced into the implant situs can include a composition adapted to promote bone growth, or enhance the attachment of the implant to the bone. Thus, the composition can be selected from the group of materials including a bone growth factor, a platelet gel, a bone morphogenic protein and bio-resorbable materials. The particular composition can be selected for its specific properties.

One benefit afforded by the temporary implants is that multiple treatments with the biological material can be applied. For instance, a platelet gel may be first infused into the bone cavity, followed by a fixation material, such as bone cement. The temporary implants of the present invention provide a significant degree of flexibility in the treatment and pre-treatment of the bone in anticipation of a permanent implant.

What is claimed is:

1. A method for securing a prosthesis within a bone having a medullary canal defined by a canal side wall, comprising the steps of:
   creating a cavity in the bone that extends at least partially into the medullary canal, the cavity being configured to receive the prosthesis therein;
   providing a temporary implant having a body that includes (i) a proximal end having an input port defined therein, (ii) an implant sidewall extending distally from said proximal end, the implant sidewall having a plurality of spaced apart output ports defined therein, each output port being in fluid communication with the input port, and (iii) a distal end possessing no output ports;
   positioning the temporary implant in the cavity so that the implant sidewall having the plurality of output ports defined therein faces the canal sidewall;
   advancing a fluent material into the input port of the temporary implant and out of the plurality of output ports of the temporary implant while the temporary implant is positioned within the cavity whereby fluent material advancing out of the plurality of output ports contacts the canal sidewall
   removing the temporary implant from the cavity after the fluent material advancing step; and
   implanting the prosthesis within the cavity after the removing step.

2. The method for securing a prosthesis according to claim 1, wherein the fluent material advancing step includes injecting fluent material under pressure into the temporary implant.

3. The method for securing a prosthesis according to claim 2, wherein the fluent material advancing step includes maintaining the material under pressure for a period of time sufficient for the material to invade bone voids within the bone opening.

4. The method for securing a prosthesis according to claim 1, wherein the fluent material is a curable material and the method further comprises the step of maintaining the temporary implant within the cavity for a period of time sufficient to allow the material to at least partially cure in situ.

5. The method for securing a prosthesis according to claim 1, wherein the fluent material includes a composition adapted to permanently fill voids and irregularities in the bone.

6. The method for securing a prosthesis according to claim 5, wherein the composition is selected from the group including a bone slurry, a bone substitute, a demineralized bone matrix, a bone paste and a bone cement.

7. The method for securing a prosthesis according to claim 1, wherein the material includes a composition adapted to promote bone growth.

8. The method for securing a prosthesis according to claim 7, wherein the composition is selected from the group including a bone growth factor, a platelet gel, a bone morphogenic protein and bio-resorbable materials.

9. The method of claim 1, wherein the temporary implant further includes a plurality of passageways that respectively couple the plurality of output ports to the input port.

10. The method of claim 1, wherein:
    the plurality of output ports includes a first output port and a second output port,
    the canal sidewall has a void defined therein,
    the positioning step includes locating the temporary implant so that (i) the first output port is positioned proximal to said void, and (ii) the second output port is positioned distal to said void.

11. A method for securing a prosthesis within a bone having a medullary canal defined by a canal side wall, comprising:
    creating a cavity in the bone that extends at least partially into the medullary canal, the cavity being configured to receive the prosthesis therein;
    providing a temporary implant having a body that includes (i) a proximal end having an input port defined therein, (ii) a distal end, and (iii) an implant sidewall extending between the proximal end and the distal end, the implant sidewall having a plurality of output ports defined therein, each output port being in fluid communication with the input port;
    positioning the temporary implant in the cavity so that the implant sidewall having the plurality of output ports defined therein faces the canal sidewall;
    advancing a fluent material into the input port of the temporary implant and out of the plurality of output ports of the temporary implant while the temporary implant is positioned within the cavity whereby fluent material advancing out of the plurality of output ports contacts the canal sidewall;
    removing the temporary implant from the cavity after the fluent material advancing step; and implanting the prosthesis within the cavity after the removing step.

12. The method of claim 11, wherein:
the plurality of output ports includes a first output port and a second output port,
the canal sidewall has a void defined therein,
the positioning step includes locating the temporary implant so that (i) the first output port is positioned proximal to said void, and (ii) the second output port is positioned distal to said void.

13. The method of claim 11, wherein the distal end of the temporary implant is configured to be free of any output ports.

14. The method of claim 11, wherein the temporary implant further includes a plurality of passageways that respectively couple the plurality of output ports to the input port.

15. The method for securing a prosthesis according to claim 11, wherein the fluent material advancing step includes injecting fluent material under pressure into the temporary implant.

16. The method for securing a prosthesis according to claim 15, wherein the fluent material advancing step includes maintaining the material under pressure for a period of time sufficient for the material to invade bone voids within the bone opening.

17. The method for securing a prosthesis according to claim 11, wherein the fluent material is a curable material and the method further comprises the step of maintaining the temporary implant within the cavity for a period of time sufficient to allow the material to at least partially cure in situ.

18. The method for securing a prosthesis according to claim 11, wherein the fluent material includes a composition adapted to permanently fill voids and irregularities in the bone.

19. The method for securing a prosthesis according to claim 18, wherein the composition is selected from the group including a bone slurry, a bone substitute, a demineralized bone matrix, a bone paste and a bone cement.

20. The method for securing a prosthesis according to claim 11, wherein the material includes a composition adapted to promote bone growth.

21. The method for securing a prosthesis according to claim 20, wherein the composition is selected from the group including a bone growth factor, a platelet gel, a bone morphogenic protein and bio-resorbable materials.

* * * * *